United States Patent [19]

Arkans

[11] Patent Number: 4,574,812

[45] Date of Patent: Mar. 11, 1986

[54] ARTERIAL THROMBUS DETECTION SYSTEM AND METHOD

[75] Inventor: Edward J. Arkans, Sunland, Calif.

[73] Assignee: The Kendall Company, Walpole, Mass.

[21] Appl. No.: 601,722

[22] Filed: Apr. 18, 1984

[51] Int. Cl.⁴ ............................................... A61B 5/02
[52] U.S. Cl. .................... 128/691; 128/694; 128/693
[58] Field of Search ........... 128/679, 680, 681, 691 E, 128/693, 694, 672, 677, 687, 689

[56] References Cited

U.S. PATENT DOCUMENTS

| | | | |
|---|---|---|---|
| 3,835,840 | 9/1974 | Mount | 128/693 |
| 3,996,924 | 12/1976 | Wheeler | 128/693 |
| 4,144,878 | 3/1979 | Wheeler | 128/693 |
| 4,166,455 | 9/1979 | Findl et al. | 128/691 |
| 4,169,463 | 10/1979 | Piquard | 128/693 |

FOREIGN PATENT DOCUMENTS

| | | | |
|---|---|---|---|
| 2751004 | 11/1976 | Fed. Rep. of Germany | 128/694 |
| 2471177 | 6/1981 | France | 128/693 |

*Primary Examiner*—Edward M. Coven
*Attorney, Agent, or Firm*—James W. Potthast

[57] ABSTRACT

An arterial thrombus detection system (4) measures and displays the elapsed times (ET1, ET2, etc.) for an arterial pulse to travel between selected pairs of locations (A and B, B and C) along the length of a patient's limb (10, 12). The arterial pulse sensors comprise inflatable cuffs (A, B, C) with pressure sensors (A, B, C) that are flexibly secured together to form a sleeve (6, 8) which is wrapped around the limb (10, 12). A pair of start/stop timers (46, 48) are controlled in accordance with arterial detection pulses to measure the elapsed times (ET1, ET2, etc.). Display of elapsed times (ET1, ET2, etc.) which are significantly different signifies a thrombus in the section of the limb associated with the relatively longest elapsed time.

20 Claims, 2 Drawing Figures

ARTERIAL THROMBUS DETECTION SYSTEM AND METHOD

BACKROUND OF THE INVENTION

This invention relates generally to a system for detection of an arterial thrombus in a patient's limb.

There is a great need for simple and reliable means for detecting the presence and location of an arterial thrombus. If detected, the thrombus can be corrected or alleviated through treatment, dietary changes or surgical procedure. If undetected, arterial thrombus can lead to severe medical problems and even death by heart attack.

Accordingly, efforts have been made to design devices and to devise methods for detecting an arterial thrombus.

In a system shown in U.S. Pat. No. 4,169,463 of Piquard, detection is attempted by comparison of the electrical impedance characteristics of a limb with preselected standard characteristics under changing conditions of artificial occlusion of the limb under study. A single sensor in the form of a resilient mercury filled tube wrapped around the limb elongates and thus changes its resistance when changing conditions of occlusion temporarily alters the volume of the limb. Similarly, in U.S. Pat. No. 4,144,878 of Wheeler, the venous patency of a human limb is assessed by measuring the venous outflow within a defined time interval after release of a forced blockage of the venous return to the heart and correlating it, where necesary, with the increased venous volume occasioned by the forced blockage. As in Piquard U.S. Pat. No. 4,169,463, the volume changes and outflow rate are determined from electrical impedance measurements.

While these systems can function to detect an arterial thrombus in a limb, their sophistication and resultant complication leads to high equipment cost, decreased reliability and increased labor cost of operation. Further, despite their sophistication, they fail to provide a simple and effective means of locating the relative position of the thrombus.

Further, to the extent that these systems depend upon average or standard physiological response for purposes of detection which are not appropriate to the individual patient under study, erroneous detection can result.

SUMMARY OF THE INVENTION

Accordingly, it is an object of the present invention to provide a system and method for detection of an arterial thrombus in which detection is based on a standard established by the patient under study instead of an artifical or external standard and in which not only the presence of a thrombus, but also the relative location of the thrombus, is detected.

I achieve this objective by providing an arterial thrombus detection system with means for sensing the passage of an arterial pulse past at least three selected locations spaced along the length of a patient's limb. The time elapsed during passage of the pulse between different pairs of the sensor locations is determined. A relationship between the elapsed times associated with the different pairs of sensors which is indicative of possible arterial thrombus is displayed. A significant difference in elapsed times for comparably spaced pairs of sensor locations suggests the possibility of an arterial thrombus in the section of the patient's limb between the pair of sensor locations having the longest elapsed time.

In a preferred embodiment, the arterial pulse sensors comprise inflatable cuffs with pressure sensors which sense the incremental changes in cuff pressure when an arterial pulse passes by. The cuffs are wrapped around or are otherwise pressed snuggly against a patient's limb, but the cuffs are not pressurized to cause any occlusions of the arteries. Instead, they are only provided with a relatively small bias pressure to ensure a sufficiently tight fit for proper response of cuff pressure to arterial pressure pulses.

Preferably, the sensors are mounted at different points along the length of a sleeve corresponding to different preselected sensor locations along the patient's limb. The sleeve supports and holds the sensors but is sufficiently flexible to allow fitting the sensors to different sized limbs.

The elapsed time determining means preferably comprises at least a pair of electronic timers and means for controlling the timers in accordance with the sensors. Each pair of sensors has a timer associated therewith which is started when the arterial pulse reaches the first sensor and is stopped when the arterial pulse reaches the second sensor.

Thus, a method for practicing of my invention is provided which is both simple and effective. The elapsed time for an arterial pulse to travel between a first pair of locations is first determined. The elapsed time for a second pair of spaced locations is then determined. A significant difference between the elapsed times of the two pairs of locations is then displayed which is indicative of a thrombus present at a point intermediate the pair of locations having the largest elapsed time associated therewith.

In the preferred embodiment in which a sleeve is provided, the patient's limb is first inserted in a sensor sleeve with at least three arterial pulse sensors. The sleeve is then arranged to place the sensors in sensing engagement with the limb at selected locations spaced therealong.

BRIEF DESCRIPTION OF THE DRAWINGS

The foregoing objects, features and advantages will be described in greater detail and further objects, features and advantages will be made apparent in the detailed description of the preferred embodiment which is given with reference to the two figures of the drawing, in which.

DETAILED DESCRIPTION

Figure 1:
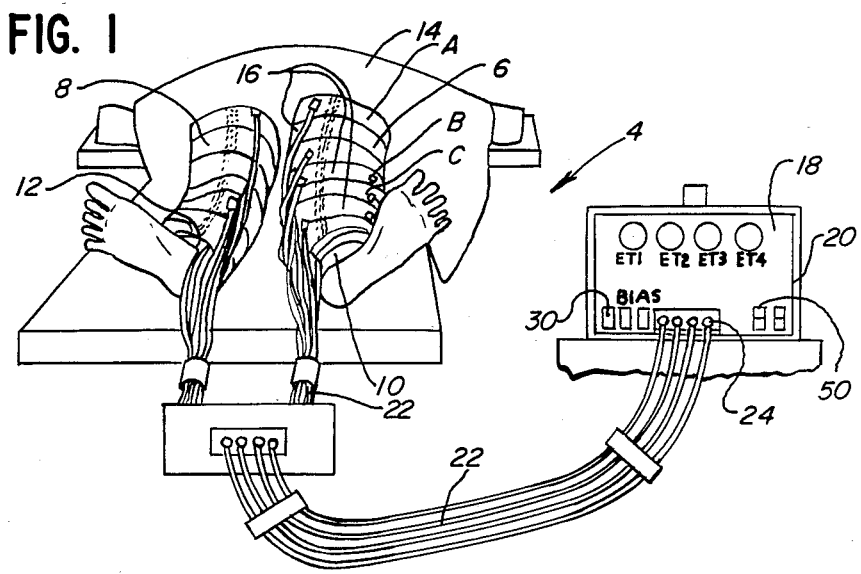
FIG. 1 is an illustrative perspective view of a preferred embodiment of the arterial thrombus detection system showing a sensor sleeve and a housing for the sensor, timer and display.

Referring now to the drawing, particularly FIG. 1, the preferred embodiment of my arterial thrombus detection system 4 is seen to include at least one of two sensor sleeves 6 and 8 for sensing arterial pulses in the limbs, or in this instance, the legs 10 and 12, of a patient 14. The sleeves 6 and 8 are identical, and each contains a plurality of identical arterial pulse sensors A, B and C at spaced selected locations along the length of the sleeve 6.

Preferably, the arterial pulse sensors A, B and C comprise, respectively, inflatable pressure cuffs A, B and C and a plurality of associated pressure sensors, or transducers, A, B and C for sensing the pressure fluctuation in the cuffs due to arterial pulses. Further explanation of pressure sensors of this general type can be obtained from U.S. Pat. Nos. 3,118,440 of DeDobbeleer; 3,157,177 of Smith, 3,348,534 of Marx et al. and 3,581,134 of Croslin. Other types of sensors could also be used. Briefly, the pressure sensors A, B and C are transducers which produce output electrical signals in response to and related to the input cuff pressure. When an arterial pulse passes through the limb at the location of the cuff, the volume of the limb expands slightly which causes the cuff pressure to slightly rise. This results in a temporary increase in the transducer electrical output signal. The peak of this signal is detected as an arterial pulse detection signal.

The inflatable cuffs A, B and C are interconnected in spaced relationship by means of relatively flexible webs 16 to form the flexible sleeve 6. The flexible webs 16 enable placement of the sensors at different selected distances between them to accommodate limbs of different size. The webs 16 also maintain the integrity of the sleeve which facilitates storage, handling sensor protection and proper placement of the pressure sensors A, B and C on the patient's limb.

After the sleeve is wrapped around the patient's limb and loosely secured by suitable fasteners (not shown), the sensors A, B and C are similarly placed at selected locations along the limb using suitable anatomical landmarks. The inflated cuffs are then slightly pressurized with a bias pressure sufficient to remove all wrinkles from the cuff but not so large as to occlude the arteries in the limb. The bias pressure is selected to be within the range of pressures through which the sensor will operate optimally to detect the arterial pulse induced cuff pressure fluctuations.

The second portion of my arterial thrombus detection system 4 comprises a control module 18 having a housing 20 within which is contained the pressure sensors A, B and C and means for pressurizing the cuffs A, B and C, detecting the arterial pulses and displaying the results of the detection procedure. The cuffs A, B and C within housing 20 are pneumatically connected to their associated sensors A, B and C within housing 20 through flexible tubes 22 and an associated connector 24 at the front panel of housing 20.

Figure 2:
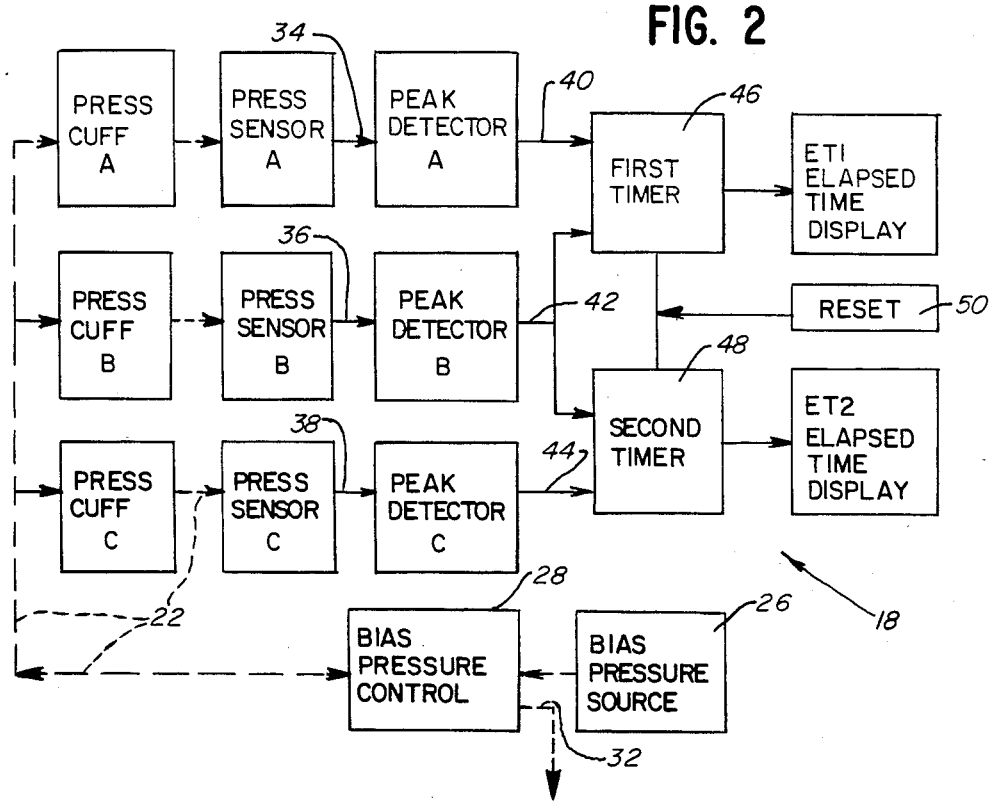
FIG. 2 is a block diagram of the sensor, timer and display electronics of the preferred embodiment.

Referring now to FIG. 2, the module 18 also includes, or is connected with, a bias pressure source 26 which is selectively connected with the pressure cuffs A, B and C through means of a bias pressure control 28 in accordance with the settings of bias pressure switches 30, FIG. 1. When actuated, the bias pressure control 28 connects the bias pressure source 26 to the pressure cuffs A, B and C. When deactuated, the bias pressure control 28 connects the pressure cuffs A, B and C to a pressure drain 32, such as atmosphere. A control of this type is conventional and thus, no detailed description is provided here. However, reference may be made to U.S. Pat. No. 4,013,069 of Hasty and some of the above referenced patents for the details of controls of this general type.

In a preferred embodiment, the arterial thrombus is detected by comparison of elapsed times for arterial pulses to travel between different pairs of sensors of the same limb. Alternately or additionally, elapsed times of different limbs are compared for an indication of a possible thrombus. Accordingly, as seen in FIG. 1, four displays ET1, ET2, ET3 and ET4 are provided for displaying the elapsed times between four pair of sensors. These four pairs of sensors may all be associated with one limb or with two diffrent limbs. However, for purposes of simplicity, the description of the operation will be given as if detection is through use of only sleeve with three sensors forming two different pairs of sensors associated with displays ET1 and ET2.

Referring to FIG. 2, the two pairs of sensors preferably share one sensor: the first pair of sensors comprise pressure sensor A and pressure sensor B, and the second pair of sensors comprise pressure sensor B and pressure sensor C. The three pressure sensors A, B and C have their electrical outputs 34, 36 and 38 connected to a peak detector A, a peak detector B and a peak detector C, respectively. These peak detectors A, B and C produce detection output pulses on their outputs 40, 42 and 44 in response to the input signals therein exceeding a preselected peak level indicative of an arterial pulse.

The detection pulses on outputs 40, 42 and 44 are used to control a first timer 46 and a second timer 48. Timer 46 and 48 preferably comprise start/stop, binary counters. The detection pulse on output 40 of peak detector A causes the first timer 46 to start timing. The detection pulse on output 42 is connected to both the first timer 46 to stop it from timing and to the second timer 48 to start it timing. The second timer 48 is stopped from further timing in response to a detection pulse on output 44 of peak detector C.

The elapsed times measured by timers 46 and 48 are respectively displayed by the ET1 elapsed time display and the ET2 elapsed time display. Preferably, these are digital displays.

After a measurement has been made, and possibly recorded either manually or automatically, the first and second timers 46 and 48 are reset to zero time by means of a manually actuated reset switch 50. The timers 46 and 48 are then ready for another elapsed time measurement. Alternately, the timers are automatically reset after a preselected time period after the second timer 48 has stopped and measurements are periodically made on an automatic basis.

While preferably the actual elapsed times are displayed regardless of whether they are significantly different, alternately only significant differences in the elapsed time indicative of a thrombus are displayed. Alternately, or additionally, the percentage differences in elapsed times or some other indication of their relationship is displayed instead of the actual elapsed times being displayed to indicate their relationship.

Thus, an effective and simple method of detecting an arterial thrombus is provided. First, the limb 10 is put in a special sleeve 6 having at least three pulse sensors A, B and C spaced therealong. The sleeve 6 is then arranged on limb 10 to place the sensors A, B and C in sensing engagement with the limb 10 at selected locations spaced therealong. The sensors A, B and C are then used to control the timers 46 and 48 to determine the elapsed time for a pulse to travel between the selected locations. After this determination is made, the indicated elapsed times are displayed to indicate any relationship between them which would be indicative of an arterial thrombus. The section of the limb between the two sensors which displays a significantly relatively greater elapsed time is the section at which the thrombus is located.

Alternately or additionally, corresponding measurements from a second limb are also compared with those of a first limb and displayed for purposes of detecting thrombus indicative relationships.

It should be appreciated that many variations can be made with respect to the preferred embodiment without departing from the scope of my invention as defined in the appended claims. For instance, although a particular type of sensor has been shown, detection of a thrombus could be achieved with other types of sensors. Also, although a sleeve is preferred for mounting the sensors, the sensors could be individually secured to the limb without a sleeve in order to make the desired elapsed time measurements. While the distance between pairs of sensors is preferably equal, they could be placed at unequal distances and the elapsed times evaluated or displayed on a proportional basis. This invention is not limited to the details of the preferred embodiment, and the above variations.

I claim:

1. An arterial thrombus detection system, comprising:
   means for sensing the passage of an arterial pulse past at least three selected locations spaced along the length of a patient's limb;
   means responsive to the sensing means to determine the time elapsed for passage of the pulse between different pairs of said selected locations; and
   means for displaying a relationship between elapsed times of different pairs of selected locations which is indicative of a possible arterial thrombus of the limb.

2. The arterial thrombus detection system of claim 1 in which said sensing means includes, in association with each selected location,
   an inflatable cuff for pressurized snug engagement with the limb at the selected location associated therewith, and
   a sensor for detecting fluctuation in the pressure of the cuff caused by an arterial pulse.

3. The arterial thrombus detection system of claim 2 in which said sensor comprises a transducer for converting pressure fluctuations into corresponding fluctuations of an electrical signal.

4. The arterial thrombus detection system of claim 1 in which sensing means includes
   an elongate sleeve for receipt therewithin of a patient's limb, and
   a plurality of sensors carried by said sleeve at different points therealong associated with said selected locations.

5. The arterial thrombus detection system of claim 4 in which
   said sleeve includes a plurality of inflatable cuffs respectively associated with said plurality of sensors, and
   each of said sensors senses the fluctuation of pressure in its associated cuff caused by passage of an arterial pulse thereby.

6. The arterial thrombus detection system of claim 4 in which said sleeve includes flexible webs between adjacent sensors.

7. The arterial thrombus detection system of claim 1 in which
   said sensing means includes a plurality of sensors for respectively sensing an arterial pulse at said selected locations, and
   each of said sensors generates an electrical pulse in response to the sensing of an arterial pressure pulse.

8. The arterial thrombus detection system of claim 7 in which the elapsed time determining means includes at least a pair of start/stop timers controlled in accordance with said electrical pulses.

9. The arterial thrombus detection system of claim 8 in which the elapsed time determining means includes
   means for starting the first timer in response to the first sensing of an arterial pulse at an upstream one of said selected locations,
   means for stopping the timing by the first timer and starting the timing by the second timer in response to sensing of the arterial pulse at the next successive selected location, and
   means for stopping the timing of the second timer in response to sensing of the arterial pulse at the second next successive selected location.

10. The arterial thrombus detection system of claim 8 including a display device associated with each of said timers for displaying an indication of the elapsed time measured by said timer.

11. The arterial thrombus detection system of claim 10 in which said elapsed time determining means includes means for resetting said timer after an elapsed time measurement has been made.

12. The arterial thrombus detection system of claim 1 in which said displaying means includes means for displaying the elapsed times associated with at least two successive pairs of said selected locations.

13. The arterial thrombus detection system of claim 1 in which
   said sensing means includes an elongate sleeve with a plurality of sensors, and
   means associated with the sleeve for enabling similar placement of the sensors relative to anatomical landmarks of different sized limbs.

14. A method of detecting an arterial thrombus in a limb, comprising the steps of:
   inserting the limb in a special sleeve having at least three arterial pulse sensors spaced along the sleeve;
   arranging the sleeve on the limb to place the sensors in sensing engagement with the limb at selected locations spaced therealong;
   determining in response to the sensors the elapsed times for an arterial pulse to travel between selected pairs of the selected locations; and
   displaying a relationship between said elapsed times indicative of an arterial thrombus.

15. The method of claim 14
   in which said sensors comprise inflatable cuffs with associated pressure sensors, and
   said step of arranging includes the step of pressuring said cuffs with a preselected bias pressure.

16. The method of claim 14 in which said step of displaying the relationship includes the step of simultaneously displaying the elapsed times of at least two of said selected pairs of locations.

17. The method of claim 14 in which said step of determining includes the step of controlling a pair of timers in response to said sensors.

18. A method of detecting an arterial thrombus in a limb, comprising the steps of:
   determining the elapsed time for an arterial pulse to travel between a first pair of locations spaced along the limb;
   determining the elapsed time for an arterial pulse to travel between a second pair of locations spaced along the limb;

displaying a relationship between the two elapsed times of the two pairs of locations indicative of an arterial thrombus present at a point intermediate the pair of locations having the relatively, proportionately largest elapsed time associated therewith.

19. The method of claim 18 in which said steps of determining include the steps of:

sensing an arterial pulse as it passes each of the pair of locations;

starting a timer in response to the pulse being sensed at the first one of the pair of locations; and stopping the timer in response to the pulse being sensed at the second one of the pair of locations to be passed by the arterial pulse.

20. The method of claim 18 in which said step of determining includes the step of controlling a timer in accordance with an arterial pulse detector.

* * * * *